United States Patent
Metcalf et al.

(10) Patent No.: US 12,268,519 B2
(45) Date of Patent: Apr. 8, 2025

(54) MOTION LIMITING APPARATUS FOR ASSESSING STATUS OF SPINAL IMPLANTS

(71) Applicant: Warsaw Orthopedic, Inc., Warsaw, IN (US)

(72) Inventors: Newton Metcalf, Memphis, TN (US); Arjun Siby Kurian, Memphis, TN (US); Nicholas Benson, Collierville, TN (US); Kevin T. Foley, Germantown, TN (US); Thomas A. Carls, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 397 days.

(21) Appl. No.: 16/855,432

(22) Filed: Apr. 22, 2020

(65) Prior Publication Data

US 2021/0330256 A1 Oct. 28, 2021

(51) Int. Cl.
*A61B 5/00* (2006.01)
*A61F 2/44* (2006.01)
*A61F 5/02* (2006.01)

(52) U.S. Cl.
CPC .......... *A61B 5/4851* (2013.01); *A61B 5/4566* (2013.01); *A61B 5/6812* (2013.01);
(Continued)

(58) Field of Classification Search
CPC ... A61B 5/4851; A61B 5/4566; A61B 5/6812; A61B 2562/0219; A61B 2562/0247;
(Continued)

(56) References Cited

U.S. PATENT DOCUMENTS 2,582,930 A * 1/1952 Jewett ..................... A61F 5/024
602/19
6,485,491 B1 11/2002 Farris et al.
(Continued)

FOREIGN PATENT DOCUMENTS

| CN | 103140168 | * | 6/2013 | |
| WO | WO-2013044157 A1 | * | 3/2013 | ........... A61B 17/025 |
| WO | WO-2020028739 A1 | * | 2/2020 | ........... A61B 5/1107 |

OTHER PUBLICATIONS

English-language machine translation of CN-103140168, pp. 1-26, 2013 (Year: 2013).*

(Continued)

*Primary Examiner* — May A Abouelela
(74) *Attorney, Agent, or Firm* — FOX ROTHSCHILD LLP (57) ABSTRACT

A system for assessing a status of a spinal implant includes a wearable apparatus having an electronics system and one or more spinal implants in communication with the wearable apparatus. The electronics system includes a first short-range receiver, a first short-range transmitter, and an inertial measurement unit. The wearable apparatus is configured to constrain one or more movements of a wearer when worn. The one or more spinal implants include one or more sensors configured to measure one or more characteristics of a fusion status of the spinal implant, a second short-range receiver, and a second short-range transmitter. The one or more spinal implants are configured to communicate one or more of the measured characteristics to the wearable apparatus via the second transmitter.

10 Claims, 8 Drawing Sheets

(52) U.S. Cl.
CPC .............. *A61F 2/4455* (2013.01); *A61F 5/02* (2013.01); *A61B 2562/0219* (2013.01); *A61B 2562/0247* (2013.01); *A61B 2562/0271* (2013.01)

(58) Field of Classification Search
CPC ........ A61B 2562/0271; A61B 2562/02; A61B 2505/09; A61B 5/6823; A61B 5/686; A61B 5/11; A61B 5/01; A61B 5/1118; A61B 5/4504; A61B 5/4519; A61B 5/6802; A61B 5/6804; A61B 5/6831; A61B 5/6878; A61F 2/4455; A61F 5/02; A61F 5/022; A61F 5/024; A61F 5/026; A61F 5/028

See application file for complete search history.

(56) References Cited

U.S. PATENT DOCUMENTS

| | | | | |
|---|---|---|---|---|
| 6,890,285 | B2* | 5/2005 | Rahman | A61B 5/4833 482/4 |
| 7,632,216 | B2* | 12/2009 | Rahman | A61B 5/4833 600/587 |
| 8,057,519 | B2 | 11/2011 | Justis et al. | |
| 11,553,969 | B1* | 1/2023 | Lang | G06T 7/0012 |
| 2010/0211106 | A1* | 8/2010 | Bowden | A61B 17/7026 606/279 |
| 2011/0060260 | A1* | 3/2011 | Siegler | A61F 5/02 602/18 |
| 2013/0118255 | A1* | 5/2013 | Callsen | A42B 3/046 73/491 |
| 2013/0150891 | A1* | 6/2013 | Dodgen | A61B 17/7026 606/260 |
| 2013/0205480 | A1* | 8/2013 | Nagely | A63B 23/025 2/425 |
| 2014/0039371 | A1* | 2/2014 | Johnson | A61F 5/02 602/19 |
| 2014/0171834 | A1* | 6/2014 | DeGoede | A61B 5/6802 600/595 |
| 2015/0133843 | A1* | 5/2015 | Turrini | A61F 5/026 602/19 |
| 2015/0182160 | A1* | 7/2015 | Kim | A61B 5/7475 600/301 |
| 2016/0317084 | A1* | 11/2016 | DeLuke | A61F 5/3738 |
| 2017/0079555 | A1 | 3/2017 | Munro et al. | |
| 2017/0173262 | A1* | 6/2017 | Veltz | G16H 20/17 |
| 2017/0325740 | A1* | 11/2017 | Barnes | A61B 5/6823 |
| 2018/0280245 | A1* | 10/2018 | Khalid | A61J 7/04 |
| 2018/0358119 | A1* | 12/2018 | Bhushan | G16H 40/63 |
| 2019/0082960 | A1* | 3/2019 | Munro | A61B 5/4566 |
| 2019/0247217 | A1 | 8/2019 | Govin et al. | |
| 2020/0022733 | A1 | 1/2020 | Benson et al. | |
| 2020/0022735 | A1 | 1/2020 | Fields et al. | |
| 2020/0022739 | A1 | 1/2020 | Benson et al. | |
| 2020/0022740 | A1 | 1/2020 | Benson et al. | |
| 2020/0022772 | A1 | 1/2020 | Benson et al. | |
| 2020/0085366 | A1* | 3/2020 | Benson | A61B 5/4566 |
| 2022/0125535 | A1* | 4/2022 | Janna | A61B 90/50 |

OTHER PUBLICATIONS

European Search Report dated Sep. 20, 2021 issued in EP 21168046.7.

* cited by examiner

MOTION LIMITING APPARATUS FOR ASSESSING STATUS OF SPINAL IMPLANTS

TECHNICAL FIELD

The present disclosure generally relates to a wearable motion limiting apparatus that is in operable communication with one or more spinal implant-based sensors to collect implant status data in association with assessment protocols, and to provide multiple stakeholders such as, for example, clinicians, patients, insurers and employers, with objective information pertaining to a patient's spinal condition.

BACKGROUND

Treatment of spinal disorders, such as degenerative disc disease, disc herniations, scoliosis or other curvature abnormalities, and fractures, often requires surgical treatments. For example, spinal fusion may be used to limit motion between vertebral members. As another example, implants may be used to preserve motion between vertebral members.

A patient's spinal condition is generally evaluated using a combination of patient feedback, imaging technologies and clinician evaluations. Since data pertaining to a patient's movement can contain valuable information about the health of the patient's neurological function and musculoskeletal health, it is desirable to obtain this information in an objective rather than subjective manner.

SUMMARY

In an embodiment, a system for assessing a status of a spinal implant includes a wearable apparatus having an electronics system and one or more spinal implants in communication with the wearable apparatus. The electronics system includes a first short-range receiver, a first short-range transmitter, and an inertial measurement unit. The wearable apparatus is configured to constrain one or more movements of a wearer when worn. The one or more spinal implants include one or more sensors configured to measure one or more characteristics of a fusion status of the spinal implant, a second short-range receiver, and a second short-range transmitter. The one or more spinal implants are configured to communicate one or more of the measured characteristics to the wearable apparatus via the second transmitter.

The electronics system may be embedded into the wearable apparatus.

Alternatively, the electronics system is configured to be removably secured to the wearable apparatus. The electronics system may include a mobile electronic device.

The inertial measurement unit may be configured to measure data pertaining to one or more assessed motions of the wearer. The wearable apparatus may be configured to transmit at least a portion of the measured characteristics and at least a portion of the data pertaining to one or more assessed motions of the wearer to an electronic device located remotely from the wearable apparatus. The electronic device may include one or more of the following: a client electronic device associated with a healthcare professional, a client electronic device associated with the wearer, or an electronic device associated with an assessment system. The one or more assessed motions may be part of a protocol.

The one or more sensors may include a load sensing assembly configured to detect a strain experienced by an associated spinal implant. The one or more sensors may include a pressure sensor. The one or more sensors may include a second inertial measurement unit. The one or more sensors may include a temperature sensor.

In an embodiment, a system for assessing a status of a spinal implant may include a wearable apparatus having an electronics system, and one or more spinal implants in communication with the wearable apparatus. The electronics system includes a first short-range receiver, and a first short-range transmitter. The wearable apparatus is configured to constrain one or more movements of a wearer when worn. The one or more spinal implants include one or more sensors configured to measure one or more characteristics of a fusion status of the spinal implant, a second short-range receiver, and a second short-range transmitter. The one or more spinal implants are configured to communicate one or more of the measured characteristics to the wearable apparatus via the second transmitter.

The electronics system may be embedded into the wearable apparatus. Alternatively, the electronics system may be configured to be removably secured to the wearable apparatus. The electronics system may include a mobile electronic device.

The wearable apparatus may include an inertial measurement unit that is configured to measure data pertaining to one or more assessed motions of the wearer. The wearable apparatus may be configured to transmit at least a portion of the measured characteristics and at least a portion of the data pertaining to one or more assessed motions of the wearer to an electronic device located remotely from the wearable apparatus.

The electronic device may include one or more of the following: a client electronic device associated with a healthcare professional, a client electronic device associated with the wearer, or an electronic device associated with an assessment system.

The one or more assessed motions may be part of a protocol.

The one or more sensors may include a load sensing assembly configured to detect a strain experienced by an associated spinal implant. The one or more sensors may include a pressure sensor. The one or more sensors may include an inertial measurement unit. The one or more sensors may include a temperature sensor.

DETAILED DESCRIPTION

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following terms shall have, for purposes of this application, the respective meanings set forth below:

A "computing device", "electronic device", or "computer" refers to a device or system that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, mobile electronic devices such as smartphones, Internet-connected wearables, tablet computers, laptop computers, and appliances and other devices that can communicate in an Internet-of-things arrangement. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion below, a client device, server device, virtual machine or container may be referred to simply as a "device" for brevity. Additional elements that may be included in electronic devices will be discussed below in the context of FIG. 6.

The terms "memory," "computer-readable medium" and "data store" each refer to a non-transitory device on which computer-readable data, programming instructions or both are stored. Unless the context specifically states that a single device is required or that multiple devices are required, the terms "memory," "computer-readable medium" and "data store" include both the singular and plural embodiments, as well as portions of such devices such as memory sectors.

Figure 1:
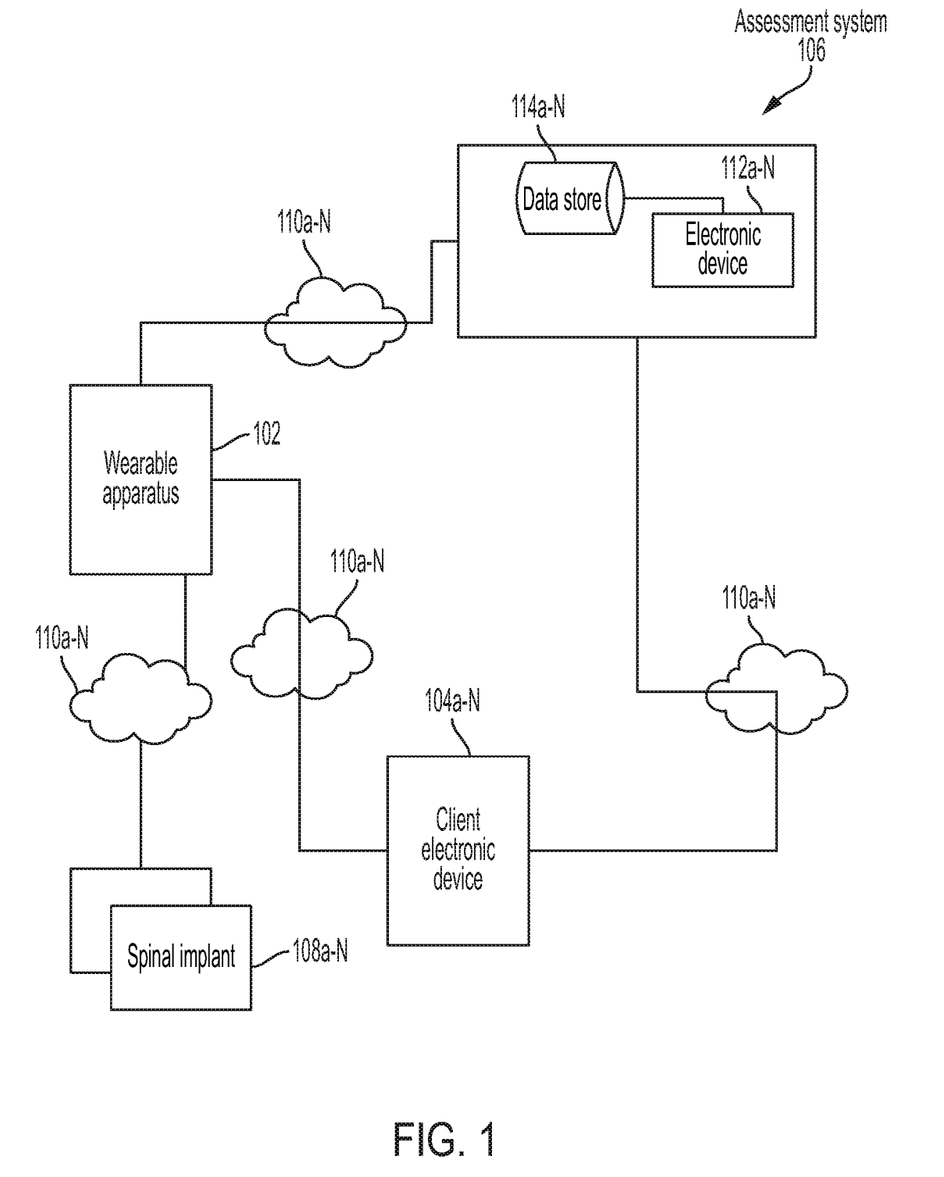
FIG. 1 illustrates an example spinal evaluation system.

FIG. 1 illustrates an example spinal evaluation system according to an embodiment. As illustrated by FIG. 1, the system 100 includes a wearable apparatus 102, one or more client electronic devices 104a-N, an assessment system 106, and one or more spinal implants 108a-N.

The wearable apparatus 102 may be in communication with one or more client electronic devices 104a-N and/or the assessment system 106 via one or more communication networks 110a-N. Similarly, a client electronic device 104a-N may be in communication with the assessment system 106 via one or more communication networks 110a-N. A communication network 110a-N may be a local area network (LAN), a wide area network (WAN), a mobile or cellular communication network, an extranet, an intranet, the Internet, a short range communication network and/or the like. Although FIG. 1 shows separate communication networks 110a-N it is to be understood that these networks, or some combination of these networks, may be implemented as a single communication network.

Figure 2:
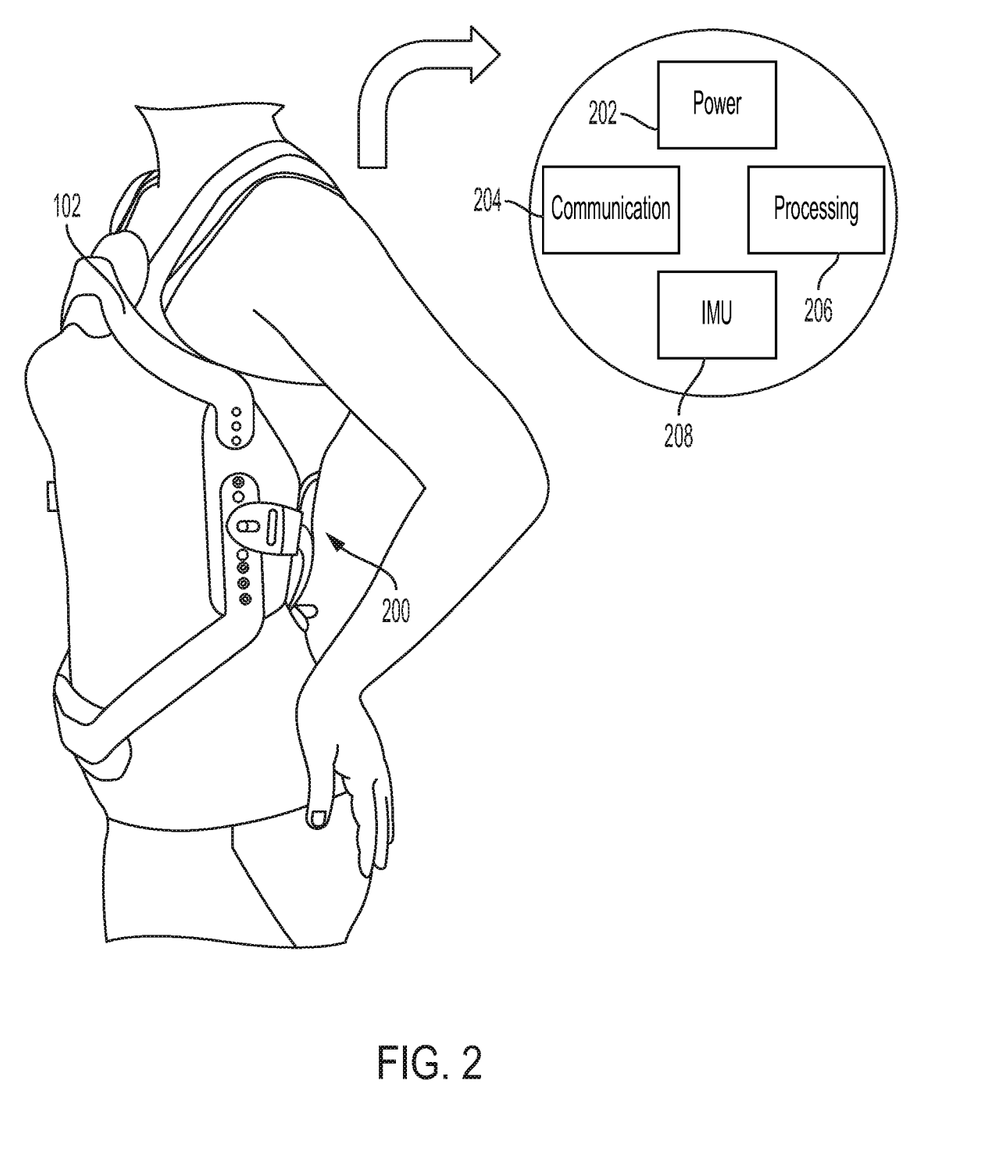
FIG. 2 illustrates an example of a wearable apparatus.

FIG. 2 illustrates an example of a wearable apparatus 102 according to an embodiment. As illustrated by FIG. 2, a wearable apparatus 102 may be a brace configured to be worn by an individual. In various other embodiments, a wearable apparatus 102 may be a belt, a harness, or other garment or apparatus. A wearable apparatus 102 may be configured to be worn by an individual across at least a portion of the individual's trunk, such as a portion of an individual's lower back, a portion of an individual's upper back, and/or anterior aspect of an individual's chest. A wearable apparatus may be secured to a subject via one or more belts, straps, fasteners, tightening mechanisms, and/or the like. U.S. patent application Ser. No. 16/132,094, which is incorporated herein by reference in its entirety, describes example wearable electronic devices and systems which may be used within the scope of this disclosure.

Figure 3A:
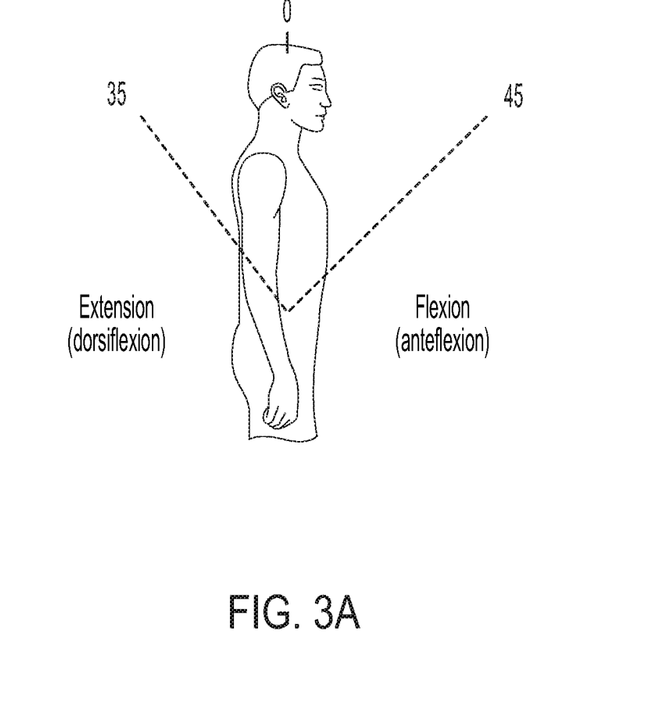
FIG. 3A illustrates example extension and flexion motion that may be constrained by a wearable apparatus.
Figure 3B:
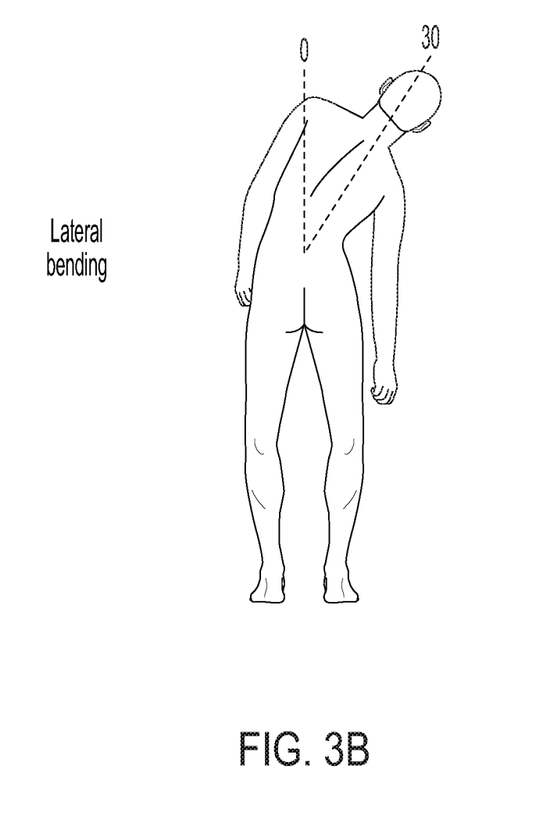
FIG. 3B illustrates example lateral bending motion that may be constrained by a wearable apparatus.
Figure 3C:
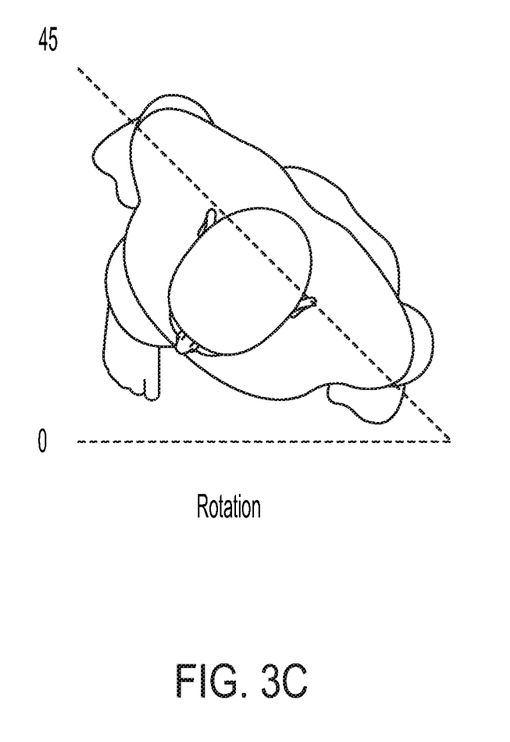
FIG. 3C illustrates example axial rotation motion that may be constrained by a wearable apparatus.

In other embodiments, a wearable apparatus 102 may be configured to be worn by an individual in order to limit one or more motions or types of motions of the individual. For example, a wearable apparatus 102, when worn by an individual, may constrain the individual's spinal motion to specific degrees of angulation in flexion and/or extension, lateral bending, and/or axial rotation. FIG. 3A illustrates example extension and flexion motion that may be constrained by a wearable apparatus. FIG. 3B illustrates example lateral bending motion that may be constrained by a wearable apparatus. FIG. 3C illustrates example axial rotation motion that may be constrained by a wearable apparatus.

In various embodiments, a wearable apparatus 102 may include an electronics system. As illustrated in FIG. 2, an electronics system 200 may be embedded into at least a portion of the wearable apparatus 102. The electronics system 200 may include a power supply 202, one or more communication components 204, one or more processing components 206, one or more inertial measurement units (IMU) 208 and/or the like.

The power supply 202 may include a battery. The communication components 204 may include one or more short-range communication components such as, for example, a short-range transmitter, receiver and/or transceiver. The communication components 204 may include one or more other communication components such as, for example, a receiver, a transmitter, and/or a transceiver that may be used to facilitate wireless communication between the electronics system 200 and one or more electronic devices over a wireless network such as, for example, the Internet or an intranet.

The processing components 206 may include one or more processing devices such as, for example, a processor, a microprocessor, and/or the like. The IMUs 208 may include one or more accelerometers, gyroscopes, magnetometers, and/or the like.

The electronics system 200 of a wearable apparatus 102 may be positioned on a portion of the wearable apparatus that overlaps at least a portion of a wearer's spine, or is near to or in proximity to a wearer's spine, when worn. For example, FIG. 2 illustrates an example placement of an electronics system 200 according to an embodiment. However, it is understood that an electronics system, or a portion of an electronics system, may be located elsewhere on the wearable apparatus.

Figure 4:
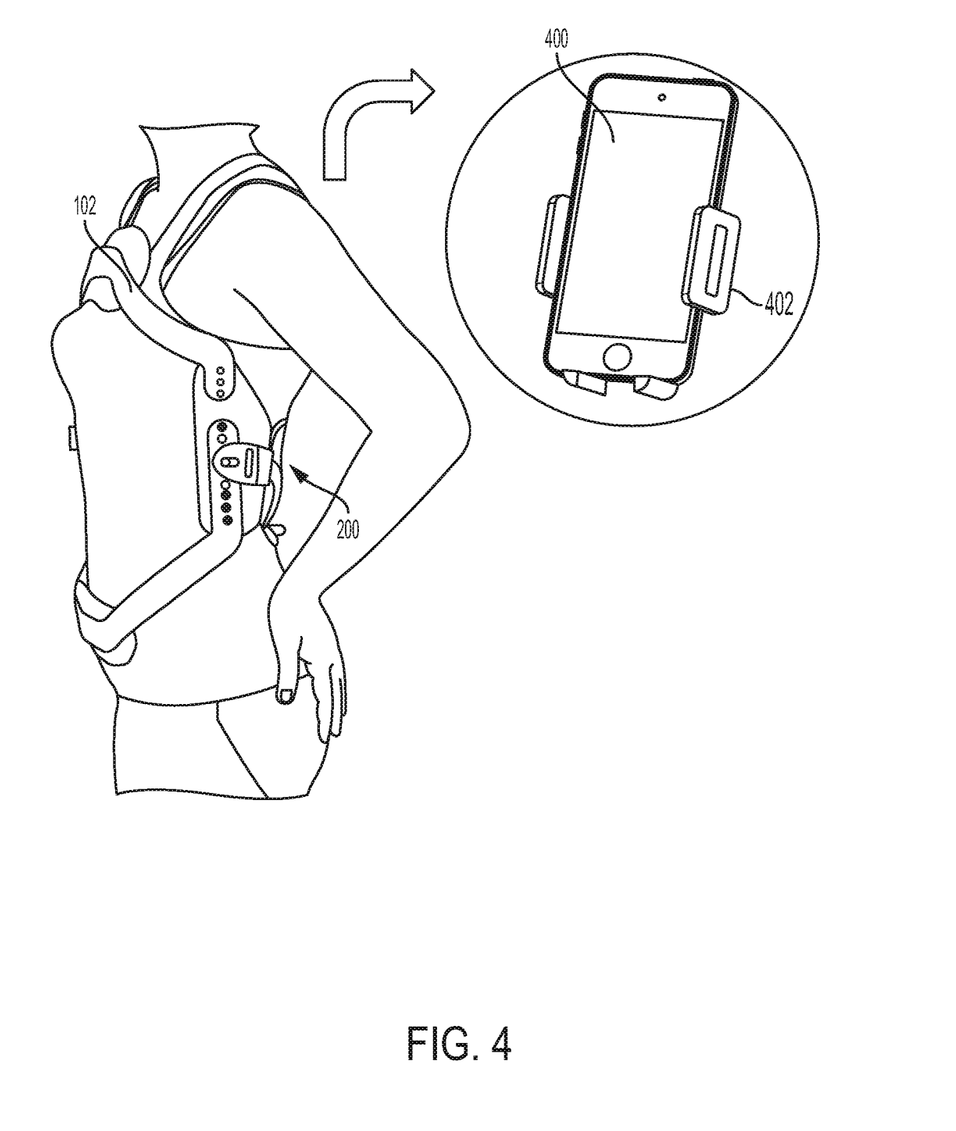
FIG. 4 illustrates an example electronics system that is removably secured to a wearable apparatus.

In various embodiments, an electronics system 200 (or at least a portion of an electronics system), may not be embedded into a wearable apparatus 102. Rather, an electronics system 200 (or portion thereof) may be a separate component that may be used with a wearable apparatus 102. In this configuration, an electronics system 200 may be removably secured to or positioned on or about a wearable apparatus 102. For example, a mobile phone or other mobile electronic device may be used as an electronics system 200. FIG. 4 provides an example illustration.

As shown in FIG. 4, a mobile electronic device 400 may be received by a holder or receptacle 402 located on a portion of the wearable apparatus 102. When the wearer has finished with the wearable apparatus 102, he or she may remove the wearable apparatus, and the mobile electronic device 400 may be removed from the wearable apparatus as well.

In various embodiments, a wearable apparatus 102 may include one or more integrated circuits, microchips or other memory devices. For instance, a wearable apparatus 102 may include a memory chip that may be removed from the wearable apparatus and inserted into another electronic device in order to transfer data stored on the memory chip. A wearable apparatus may also include firmware and/or a battery, including for example a thin film battery that may be encapsulated or may include a piezo-electronic powering.

Referring back to FIG. 1, in various embodiments, the wearable apparatus 102 may be in communication with one or more spinal implants 108a-N. A spinal implant may be a medical device used for the treatment of one or more musculoskeletal disorders. Examples of spinal implants 108a-N may include, without limitation, vertebral fixation screws, pedicle screws, hooks, cross connectors, offset connectors and related systems for use during various spinal procedures or other orthopedic procedures and that may be used in conjunction with other devices and instruments related to spinal treatment, such as rods, wires, plates, intervertebral implants, and other spinal or orthopedic implants, insertion instruments, specialized instruments such as, for example, delivery devices (including various types of cannula) for the delivery of these various spinal or other implants to the vertebra or other areas within a subject in various directions, and/or a method or methods for treating a spine, such as open procedures, mini-open procedures, or minimally invasive procedures. A spinal implant 108a-N may include one or more sensors. A sensor may be configured to detect and/or measure one or more characteristics associated with the spinal implant 108a-N. Example sensors include, without limitation, a load sensing assembly for detecting the strain experienced by a spinal implant. U.S. patent application Ser. Nos. 16/039,592, 16/395,212, 16/395,216, 16/395,221, and 16/509,285, each of which is incorporated herein by reference in its entirety, describe example load sensing assemblies which may be used within the scope of this disclosure. Other examples of sensors may include, without limitation, a pressure sensor, a temperature sensor, an IMU, a gyroscope, and/or the like.

U.S. Pat. Nos. 6,485,491 and 8,057,519, as well as U.S. patent application Ser. Nos. 16/039,592, 16/395,212, 16/395,216, 16/395,221, and 16/509,285, each incorporated herein by reference in its entirety, describe example spinal implants that may be used within the scope of this disclosure. Other example spinal implants may include, without limitation, interbody fusion devices such as, for example, fusion cages.

A spinal implant 108a-N may include a receiver, a transmitter, and/or a transceiver. A receiver, a transmitter, and/or a transceiver may be a near-field communication (NFC) or other short-range communication receiver, transmitter, and/or transceiver such as, for example, a radio frequency identification (RFID) coil, an NFC antenna, and/or the like. In various embodiments, a receiver, transmitter, and/or transceiver may be part of an integrated circuit such as, for example, an RFID chip, and NFC chip, and/or the like.

An assessment system 106 may include one or more electronic devices such as, for example, servers and/or one or more data stores. For instance, as shown in FIG. 1, an assessment system 106 may include one or more electronic devices 112a-N and one or more data stores 114a-N. A data store 114a-N may store measured data that is received from one or more sensors such as, for example, movement data, spinal implant performance information, and/or the like. A data store 114a-N may store movement information that it receives from a wearable apparatus 102. A data store 114a-N may store data so that it is correlated to a particular subject.

In various embodiments, one or more sensors of a spinal implant 108a-N may measure one or more effects of a subject's movement on the spinal implant. This movement or motion may be of a wearer's spinal axis, lower limbs and/or the like.

A client electronic device 104a-N may be a smartphone, a tablet, a laptop, a computing device or other electronic device. For instance, a client electronic device 104a-N may be a smartphone or tablet associated with a subject. As another example, a client electronic device 104a-N may be a smartphone or tablet associated with a clinician, healthcare provider, healthcare entity and/or the like.

Figure 5:
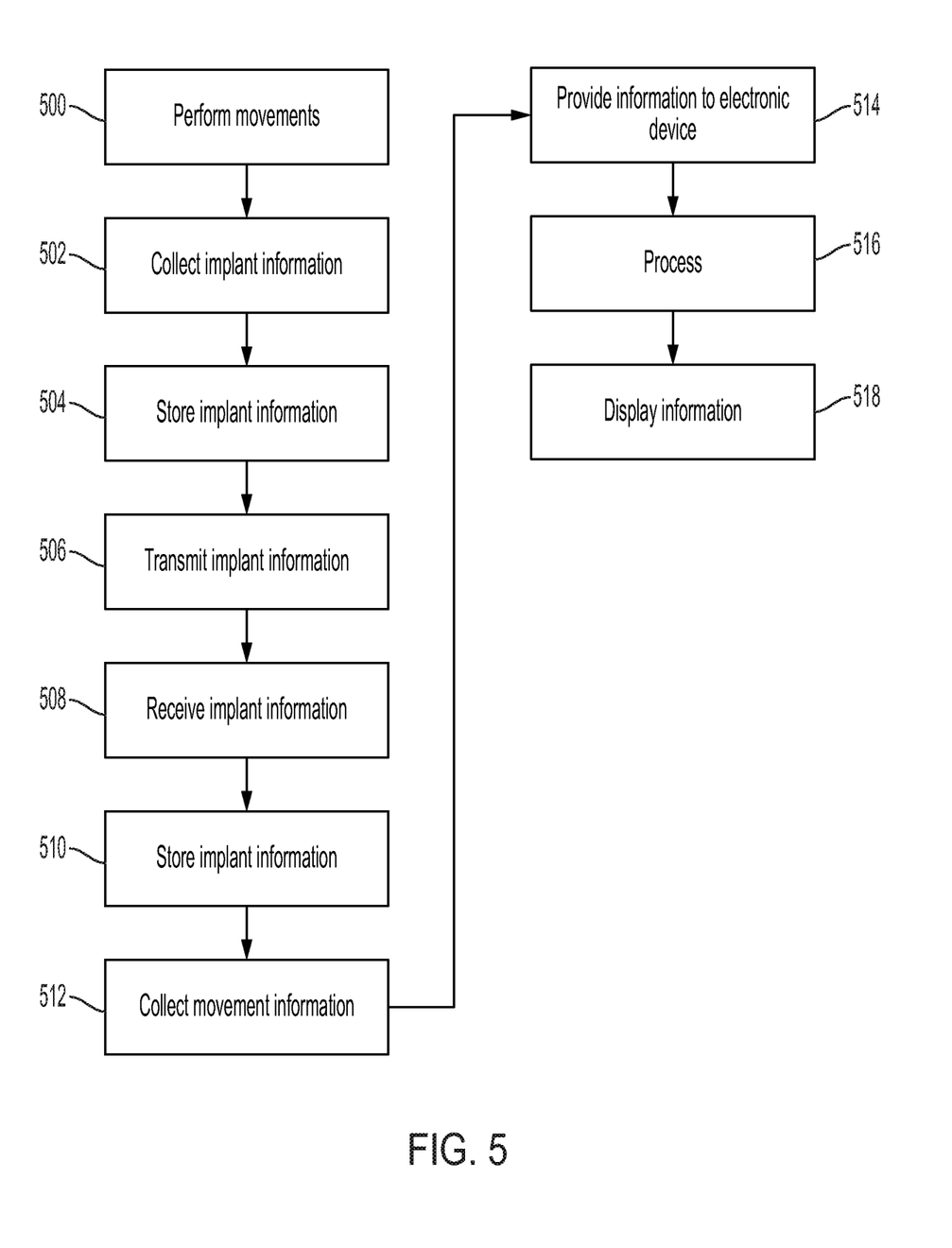
FIG. 5 illustrates a flow chart of an example method of obtaining subject information.

FIG. 5 illustrates a flow chart of an example method of obtaining subject information according to an embodiment. A subject may put on a wearable apparatus. The subject may then perform 500 one or more movements or types of movements while wearing the wearable apparatus.

A subject may wear a wearable apparatus for a limited period of time, such as, for example, in a clinical setting, during an evaluation with a clinician, and/or the like. In this situation, a subject may be asked to perform one or more movements, activities or protocols to gather information about the subject's movement. For instance, a clinician may ask a subject to sit, stand, walk, bend over, rotate, turn, lay down or perform other activities while wearing a wearable apparatus. The wearable apparatus may restrict or constrain movement of the subject so that only a certain range of motion is performed.

While the subject is performing one or more movements, one or more sensors of one or more spinal implants implanted within the subject may measure or collect 502 implant information pertaining to one or more characteristics of the associated spinal implant during such movements. For example, a spinal implant may include one or more strain gauges or strain sensors. These sensors may measure strain or one or more strain patterns experienced by the implant during one or more movements or across a range of movements. As another example, a spinal implant may include an IMU which may measure movement information during one or more movements or across a range of movements. In another example, a spinal implant may include a gyroscope which may measure an orientation of a wearer's back or trunk. In another example, a spinal implant may include a pressure sensor that may measure pressure variations on or within the spinal implant. For instance, a set screw of a spinal implant may include a pressure sensor which may measure pressure and/or pressure variations in the chamber of the implant. In another embodiments, a spinal implant may include a temperature sensor which may measure the temperature or temperature variations of the spinal implant or of the area around the spinal implant. Additional and/or alternate sensors and/or measurements may be used and/or made within the scope of this disclosure.

The spinal implants may store 504 such, and may transmit 506 at least a portion of such implant information to the wearable apparatus. Alternatively, a spinal implant may transmit 506 at least a portion of collected or measured implant information to the wearable apparatus without storing it. A spinal implant may transmit implant information to a wearable apparatus via a short-range transmitter or transceiver.

The wearable apparatus may receive 508 implant information from one or more spinal implants. For example, a wearable apparatus may receive 508 implant information from a spinal implant via a short-range receiver or transceiver. In various embodiments, a wearable apparatus may store 510 at least a portion of implant information received from one or more spinal implants. A wearable apparatus may store 510 at least a portion of received implant information in one or more data stores.

A wearable apparatus may collect or measure 512 movement information. Movement information may include one or more characteristics associated with a subject's movement. For example, an IMU may provide information pertaining to the motion of the person wearing the wearable apparatus given the IMU and its placement. The raw x/y/z measurements may, for example, provide only information about the movement of the sensor itself, which may be different from the movement of a wearer. For example, known approaches utilize motion sensors that are integrated into devices such as phones and watches, which move considerably different ways and ways that are independent of their wearers or carriers.

One or more data points of data may have one or more associated parameters such as an associated timestamp, an associated velocity value, an associated barometric pressure value, and associated acceleration value, a rotation value, an orientation value and/or the like.

At least a portion of the movement information and/or the implant information may be provided to 514 an electronic device. In an embodiment, movement information and/or implant information may be provided to an electronic device by removing a memory chip or other data store from a wearable apparatus, and connecting it to an electronic device. Alternatively, a wearable apparatus (or an electronics system associated with a wearable apparatus) may transmit at least a portion of collected implant information and/or movement information to an electronic device via one or more communication networks. In some embodiments, a wearable apparatus may transmit information to an electronic device at certain times or intervals. In other embodiments, a wearable apparatus may transmit information to an electronic device in response to receiving a request from the electronic device.

The electronic device may be located remotely from the wearable apparatus. The electronic device may be associated with a healthcare professional, a wearer of the wearable apparatus, an assessment system, and/or the like.

One or more electronic devices, such as ones associated with an assessment system, may process 516 at least a portion of the implant information and/or the movement information. In various embodiments, an electronic device may process 516 information to assess one or more characteristics or a status of a spinal implant. Characteristics may be indicative of one or more anomalies or potential issues with one or more spinal implants. For instance, information may be used to determine whether an implant is experiencing unusual or anomalous strain during certain movements. The information may be used to detect a fusion status of a subject's spine, whether a spinal implant has failed or malfunctioned, and/or the like. This information may provide valuable insight into the construct and fusion status of an implant.

For example, as a successful spinal implant fusion matures, there is less strain on the hardware of the implant because the bone takes on the load from the implant. If the spinal implant is still experiencing a certain strain level or strain pattern after a certain period of time, it may be a sign of an issue with the fusion status of the implant.

As another example, if a spinal implant is experiencing pressure that exceeds a certain threshold value or is outside of a range of expected values, this may be an indication that there is swelling around the implant. Similarly, if a temperature sensor of a spinal implant measures a temperature that exceeds a certain threshold value or is outside of a range of values, this may be an indication of an infection in an area around the spinal implant.

In various embodiments, an assessment system may cause information pertaining to one or more characteristics or status of a spinal implant to be displayed 518 on one or more electronic devices. For instance, an assessment system may cause an indication of a spinal implant that is experiencing atypical characteristics to be displayed on a tablet associated with the subject's clinician. The displayed information may include one or more measurements from one or more of the spinal implant sensors such as, for example, strain measurements, pressure measurements, temperature measurements, and/or the like. A clinician may use the information to determine whether any changes to any spinal implant need to be made, or to make other treatment recommendations for the wearer.

Figure 6:
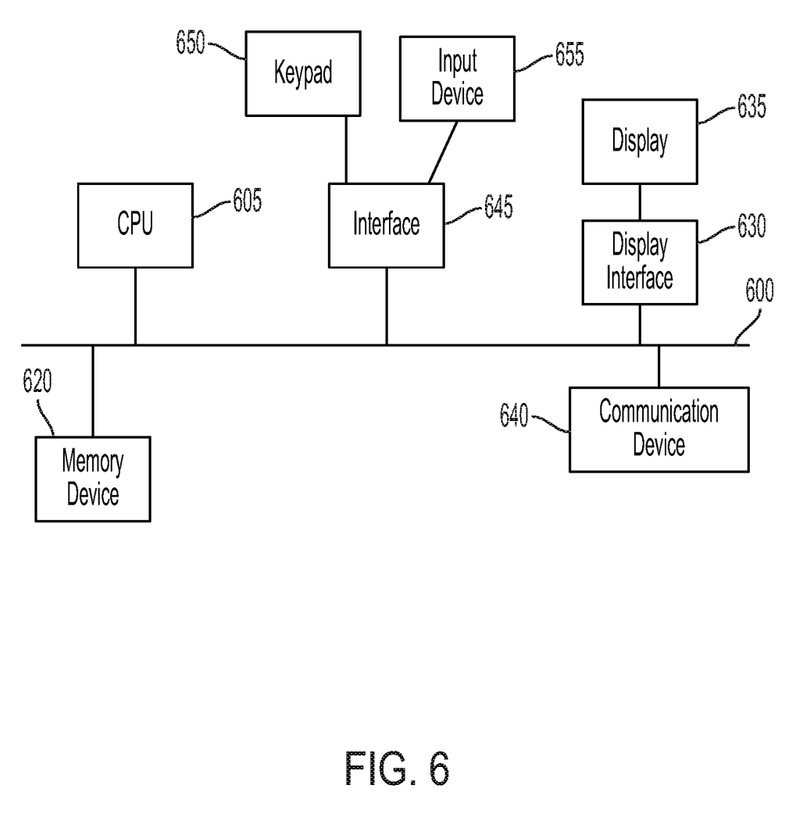
FIG. 6 depicts a block diagram of an example of internal hardware that may be used to contain or implement program instructions according to an embodiment.

FIG. 6 illustrates example hardware that may be used to contain or implement program instructions. A bus 600 serves as the main information highway interconnecting the other illustrated components of the hardware. CPU 605 is the central processing unit of the system, performing calculations and logic operations required to execute a program. CPU 605, alone or in conjunction with one or more of the other elements disclosed in FIG. 6, is an example of a processor as such term is used within this disclosure. Read only memory (ROM) and random access memory (RAM) constitute examples of non-transitory computer-readable storage media 620, memory devices or data stores as such terms are used within this disclosure.

Program instructions, software or interactive modules for providing the interface and performing any querying or analysis associated with one or more data sets may be stored in the memory device 620. Optionally, the program instructions may be stored on a tangible, non-transitory computer-readable medium such as a compact disk, a digital disk, flash memory, a memory card, a USB drive, an optical disc storage medium and/or other recording medium.

An optional display interface 630 may permit information from the bus 600 to be displayed on the display 635 in audio, visual, graphic or alphanumeric format. Communication with external devices may occur using various communication ports 640. A communication port 640 may be attached to a communications network, such as the Internet or an intranet.

The hardware may also include an interface 645 which allows for receipt of data from input devices such as a keypad 650 or other input device 655 such as a touch screen, a remote control, a pointing device, a video input device and/or an audio input device.

It will be appreciated that the various above-disclosed and other features and functions, or alternatives thereof, may be desirably combined into many other different systems or applications or combinations of systems and applications. Also that various presently unforeseen or unanticipated alternatives, modifications, variations or improvements therein may be subsequently made by those skilled in the art which are also intended to be encompassed by the following claims.

What is claimed is:

1. A system comprising:
    an electronic device configured to be associated with a healthcare professional;
    a wearable apparatus comprising an electronics system positioned on a portion of the wearable apparatus, wherein the electronics system comprises:
        an inertial measurement unit that is configured to measure data, based on a position of the inertial measurement unit on the wearable apparatus, the data pertaining to one or more assessed motions of a wearer of the wearable apparatus, the inertial measurement unit configured to measure the data pertaining to the one or more assessed motions of the wearer in each of three orthogonal directions;
        a first short-range receiver, and
        a first short-range transmitter;
    wherein the wearable apparatus is configured to be worn across at least a portion of the wearer's lower back;
    wherein the wearable apparatus, when worn by the wearer, is configured to constrain spinal motion of the wearer to specific degrees of angulation between vertebral members in flexion, extension, lateral bending, and/or axial rotation during the one or more assessed motions performed by the wearer, and
    wherein the wearable apparatus is configured to transmit information to the electronic device located remotely from the wearable apparatus, the information comprising at least a portion of the inertial measurement unit data pertaining to the one or more assessed motions performed by the wearer as part of a defined clinical evaluation protocol of the healthcare professional; and
    one or more spinal implants in communication with the wearable apparatus, wherein the one or more of the spinal implants comprises:
        one or more sensors configured to measure one or more characteristics of a fusion status of the respective spinal implant,
        a second short-range receiver, and
        a second short-range transmitter,
    wherein the one or more spinal implants are configured to communicate one or more of the measured characteristics to the wearable apparatus via the second transmitter;
    wherein the information transmitted from the wearable apparatus to the remotely located electronic device further comprises the one or more characteristics of the fusion status of the respective spinal implant communicated from the one or more spinal implants to the wearable apparatus,
    wherein the wearable apparatus is configured to receive the one or more characteristics of the fusion status from the spinal implants and measure the data pertaining to the one or more assessed motions of the wearer while the wearer performs the assessed motions and while the wearable apparatus constrains spinal motion of the wearer, and
    wherein the electronic device is configured to receive the information transmitted from the wearable apparatus and to display the received information, comprising:
        the portion of the inertial measurement unit data pertaining to the one or more assessed motions performed by the wearer; and
        the measured one or more characteristics of the fusion status communicated from the one or more spinal implants during the one or more assessed motions performed by the wearer.

2. The system of claim 1, wherein the electronics system is embedded into at least the portion of the wearable apparatus.

3. The system of claim 1, wherein the electronics system is configured to be removably secured by a holder or receptacle located on the portion of the wearable apparatus.

4. The system of claim 3, wherein the electronics system comprises a mobile electronic device.

5. The system of claim 1, wherein the electronic device is further configured to transmit the information to one or more of the following:
    a client electronic device associated with the wearer; or
    an electronic device associated with an assessment system.

6. The system of claim 1, wherein the one or more sensors comprises a load sensing assembly configured to detect a strain experienced by the respective spinal implant.

7. The system of claim 1, wherein the one or more sensors comprises a pressure sensor.

8. The system of claim 1, wherein the one or more sensors comprises a temperature sensor.

9. The system of claim 1, wherein the inertial measurement unit comprises one or more gyroscopes configured to measure the data pertaining to the one or more assessed motions of the wearer.

10. The system of claim 1, wherein the data pertaining to the one or more assessed motions of the wearer in each of three orthogonal directions comprises data pertaining to the one or more assessed motions of the wearer along x, y, and z axes.

* * * * *